United States Patent [19]

Bergmann

[11] Patent Number: 6,110,450

[45] Date of Patent: Aug. 29, 2000

[54] HAIR CARE COMPOSITIONS COMPRISING CERAMIDE

[75] Inventor: Wolfgang Robert Bergmann, Long Grove, Ill.

[73] Assignee: Helene Curtis, Inc., Chicago, Ill.

[21] Appl. No.: 09/153,471

[22] Filed: Sep. 15, 1998

[51] Int. Cl.[7] ............................... A61K 7/06; A61K 7/075
[52] U.S. Cl. ....................... 424/70.11; 424/70.1; 424/401
[58] Field of Search .................................... 424/401, 70.1, 424/70.11

[56] References Cited

U.S. PATENT DOCUMENTS

| | | | |
|---|---|---|---|
| 5,118,507 | 6/1992 | Clement | 424/401 |
| 5,236,950 | 8/1993 | Aoyama et al. | 514/478 |
| 5,693,677 | 12/1997 | Lambers et al. | . |
| 5,925,364 | 7/1999 | Ribier et al. | 424/401 |

FOREIGN PATENT DOCUMENTS

| | | |
|---|---|---|
| 0278505 | 8/1988 | European Pat. Off. . |
| 0521647 | 1/1993 | European Pat. Off. . |
| 196 27 931 | 1/1998 | Germany . |
| 97/3457097 | 9/1997 | WIPO . |

*Primary Examiner*—Thurman K. Page
*Assistant Examiner*—Amy E. Pulliam
*Attorney, Agent, or Firm*—Matthew Boxer

[57] ABSTRACT

Composition for the treatment and protection of hair, comprising, in a cosmetically acceptable medium, at least one ceramide and/or glycoceramide and phytantriol.

2 Claims, No Drawings

HAIR CARE COMPOSITIONS COMPRISING CERAMIDE

SUMMARY OF THE INVENTION

The present invention relates to compositions intended for the treatment and protection of hair and comprising, in a cosmetically acceptable medium, at least one ceramide and/or glycoceramide and phytantriol. The compositions of the invention have excellent hair conditioning properties as could be proven in salon blitz testing. The compositions of the invention can be used to treat hair to give good wet combing properties and this could be proven by using the Instron test methods set forth herein.

The invention also relates to the cosmetic treatment process employing such compositions.

Hair-care formulations which make it possible to treat hair which has been damaged by inclement weather or by unsuitable hair treatments are already known in the prior art. Cationic polymers which have the advantage of improving these cosmetic properties, inter alia, the disentangling and the softness of wet and dried hair, and also of protecting the hair fibers from these harmful agents, have already been used for this purpose. However, some cationic polymers have unsatisfactory disentangling properties, and have a tendency, for example, when treatments are superposed, to make the hair lank and feel coarse.

Ceramides or glycoceramides which have already been combined with cholesterol esters for the purpose of protecting the hair fiber are also known. Application of these latter compositions or of ceramides alone to the hair result, however, in cosmetic performance parameters which are inadequate, both on wet hair and on dried hair. The present invention relates to a combination of ceramides at least one ceramide and/or glycoceramide and phytantriol which results in especially advantageous cosmetic properties, in particular as regards wet disentangling. In particular, the combination is believed to have a synergistic effect which is not simply the addition of the properties of the two components.

The invention relates to obtaining this effect by combining ceramides or glycoceramides with phytantriol.

The present invention is therefore drawn to a composition intended for the treatment and protection of hair, based on one ceramide and/or glycoceramide and phytantriol.

The present invention is also drawn to a process for the cosmetic treatment of hair, employing such a composition.

Other subjects of the invention will become apparent on reading the description and the examples which follow.

The composition intended for the treatment and protection of hair according to the invention is essentially characterized in that it contains, in a cosmetically acceptable medium, at least one ceramide and/or glycoceramide and phytantriol.

Silicone polymers such as dimethiconol or dimethicone may also be included in the compositions of the invention.

A surfactant such as sodium lauryl ether sulfate may also be included in compositions of the invention.

A suspending agent such as Carbopol 980 may also be included in compositions of the invention.

An amphoteric surfactant such as cocamidopropyl betaine may also be included in compositions of the invention.

A polyhydric alcohol such as propylene glycol may also be included in compositions of the invention.

A cationic polymer such as Jaguar C13S may also be included in compositions of the invention.

A amphoteric surfactant such as polyglucose may also be included in compositions of the invention.

A fatty alcohol such as cetyl alcohol may also be included in compositions of the invention.

An amidoamine compound such as stearamidyl propyl dimethylamine may be used in the compositions of the invention.

A silicone polymer such as dimethicone may be used in the compositions of the invention.

Other optional ingredients include preservatives, fragrances, colors, salts and acid or bases to adjust the pH as desired.

DETAILED DESCRIPTION OF THE INVENTION

Unless otherwise indicated, as used herein, % or wt %, means weight %.

The ceramides and/or glycoceramides are known per se, and are natural or synthetic molecules corresponding to the general formula:

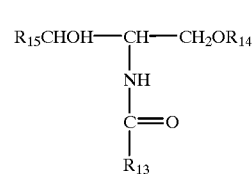

in which:

$R_{13}$ denotes a saturated or unsaturated, linear or branched alkyl radical derived from C14–C30 fatty acids, it being possible for this radical to be substituted with a hydroxyl group at the alpha-position or a hydroxyl group at the omega-position esterified with a saturated or unsaturated C16–C30 fatty acid;

$R_{14}$ denotes a hydrogen atom or a (glycosyl)$_n$, (galactosyl)$_m$ or sulphogalactosyl radical; in which:

n is an integer varying from 1 to 4; and m is an integer varying from 1 to 8;

$R_{15}$ denotes a C15–C26 hydrocarbon radical, saturated or unsaturated at the alpha-position and which can be substituted with one or more C1–C14 alkyl radicals; in the case of natural ceramides or glycoceramides, $R_{15}$ can also denote a C15–C26 alpha-hydroxyalkyl radical, the hydroxyl group being optionally esterified with a C16–C30 alpha-hydroxy acid.

Preferred ceramides are those described by Downing in Arch. Dermatol, Vol. 123, 1381–1384, 1987, or those described in French Patent FR-2,673,179, the disclosure of which is hereby incorporated by reference, the structures of which can be the following:

Ceramide 1
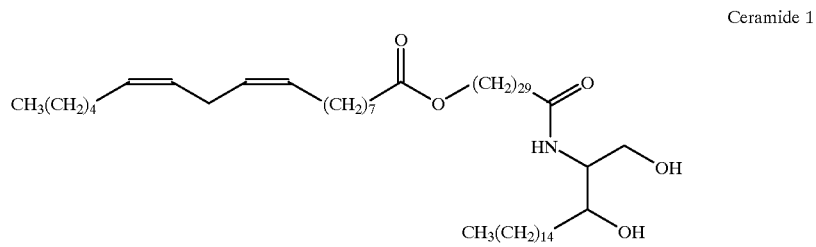
Ceramide 2
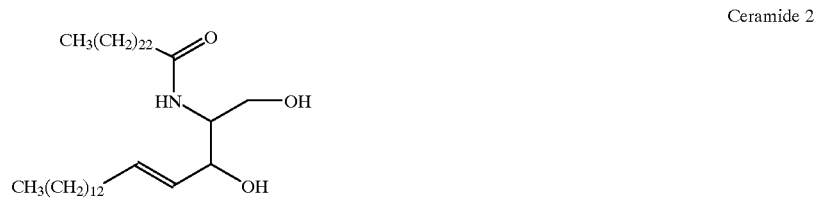
Ceramide 3
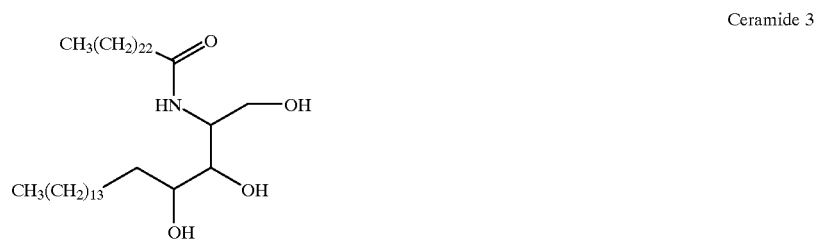
Ceramide 4
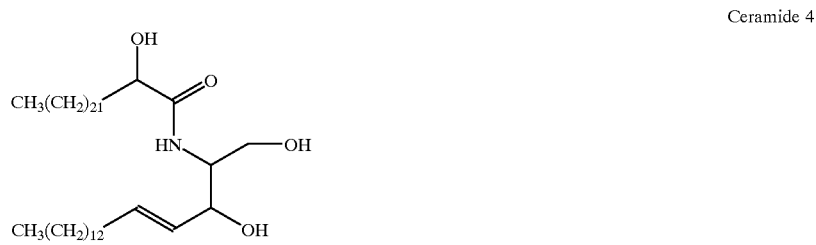
Ceramide 5
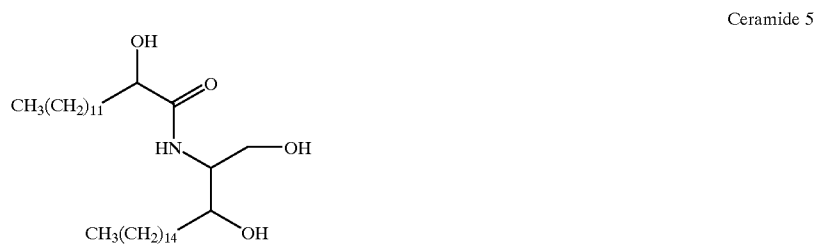
Ceramide 6I
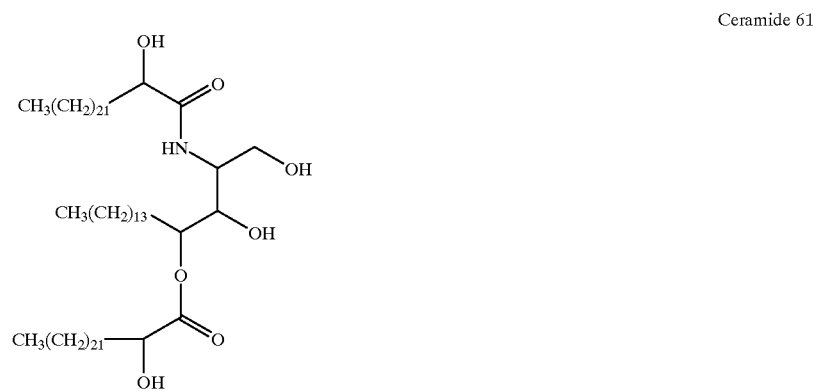

Ceramide 611

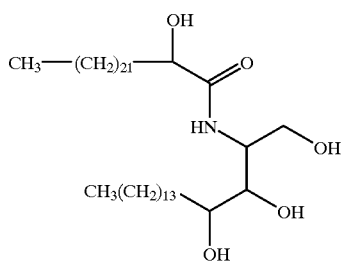

Other ceramides are ceramide 3 derivatives as described in U.S. Pat. No. 5,693,677 issued Dec. 2, 1997, which is hereby incorporated by reference.

More especially preferred, ceramides are the compounds of formula (I) above for which: $R_3$ denotes a saturated or unsaturated alkyl derived from a C16–C22 fatty acid; $R_{14}$ denotes hydrogen;

$R_{15}$ denotes a saturated linear $C_{15}$ radical.

Such compounds are, for example:
—N-linoleoyldihydrosphingosine,
—N-oleoyldihydrosphingosine,
—N-palmitoyidihydrosphingosine,
—N-stearoyidihydrosphingosine,
—N-behenoyidihydrosphingosine,
or mixtures of these compounds.

It is also preferable to use those for which:
$R_{13}$ denotes a saturated or unsaturated alkyl radical derived from a fatty acid;
$R_{14}$ denotes galactosyl or sulphogalactosyl; and
$R_{15}$ denotes —CH=CH—$(CH_2)_{12}$—$CH_3$.

The product consisting of a mixture of these compounds, sold under the trade name GLYCOCER by the company WAITAKI INTERNATIONAL BIOSCIENCES may be mentioned.

The cationic polymers are preferably used in proportions of 0.05 to 5% by weight expressed as active substance, and preferably from 0.1 to 3% by weight, relative to the total weight of the composition.

The ceramides and/or glycoceramides are preferably used in proportions of 0.005% to 5% by weight expressed as active substance, and preferably from 0.01 to 3% by weight, relative to the total weight of the composition. These compositions can contain surfactants, such as nonionic or cationic surfactants, in proportions generally from 0.1 to 10% by weight.

Phytantriol is a triol known from published German patent application No. 1,149,700, and called 3, 7, 11, 15-tetramethyl-1,2,3-trihydroxyhexadecane (also known as dihydro-2,3-dihydroxyphytol). The disclosure of German patent application No. 1,149,700 is hereby incorporated by reference.

Nonionic surfactants used in a preferred embodiment of the invention are known per se, and may be chosen from polyethoxylated, polypropoxylated or polyglycerolated alcohols, alpha-diols, alkylphenols and fatty acids having a fatty chain containing 8 to 18 carbon atoms, it being possible for the number of ethylene oxide and propylene oxide groups to range especially from 2 to 50 and for the number of glycerol groups to range, in particular, from 2 to 30.

There may also be mentioned copolymers of ethylene oxide and propylene oxide, condensates of ethylene oxide and propylene oxide with fatty alcohols; polyethoxylated fatty amides preferably having 2 to 30 mol of ethylene oxide, polyglycerolated fatty amides containing on average 1 to 5 glycerol groups, and especially 1.5 to 4 glycerol groups; polyethoxylated fatty amines preferably having 2 to 3 mol of ethylene oxide; oxyethylenated fatty acid esters of sorbitan having from 2 to 30 mol of ethylene oxide, fatty acid esters of sucrose, fatty acid esters of polyethylene glycol, alkylpolyglycosides, N-alkylglucamine derivatives and amine oxides such as (C10–C14 alkyl)amine oxides or N-acylaminopropylmorpholine oxides. Alkylpolyglycosides and polyglycerolated alcohols, alpha-diols, alkylphenols and fatty acids are more especially preferred.

The compositions according to the invention can contain cationic surfactants, such as primary, secondary or tertiary fatty amine salts, optionally polyoxyethylenated; quaternary ammonium salts such as tetraalkylammonium, alkylamidoalkyltrialkylammonium, trialkylbenzylammonium, trialkylhydroxyalkylammonium or alkylpyridinium chlorides or bromides; or imidazoline derivatives.

The compositions can contain thickening agents such as sodium alginate, gum arabic, cellulose derivatives such as methylcellulose, hydroxymethylcellulose, hydroxyethylcellulose hydroxypropylcellulose or hydroxypropylmethylcellulose guar gum or its derivatives, xanthan gums, scleroglucans, cross-linked polyacrylic acids, polyurethanes or copolymers based on optionally cross-linked maleic acid or anhydride, associative thickeners bearing fatty chains of the natural type, such as the product marketed under the name NATROSOL PLUS, or synthetic thickeners such as the products marketed under the name PEMULEN.

The pH of these compositions is generally from 2 to 9, and preferably from 3 to 8. It is adjusted with cosmetically acceptable alkalinizing or acidifying agents which are known per se.

The compositions according to the invention can contain preservatives, sequestering agents, emollients, foam modifiers, acidifying or alcalinizing agents, perfumes, colorants, viscosity modifiers, pearlescent agents, hydrating agents, antidandruff agents, antiseborrhoeic agents, sunscreen agents, proteins, vitamins, hydroxy acids, salts, detoxifying agents, permanent-waving reducing or fixing agents or mixtures thereof.

Other conditioning agents may be used in addition. In this connection, there may be mentioned natural, hydrogenated or unhydrogenated, synthetic or non-synthetic hydrocarbon oils which are cyclic or aliphatic, linear or branched, saturated or unsaturated and soluble or insoluble, fatty alcohols; volatile or non-volatile silicones, organomodified or otherwise and soluble or insoluble in the medium; perfluorinated or fluorinated oils, polybutenes and polyisobutenes, fatty esters occurring in liquid, pasty or solid form, esters of polyhydric alcohols, glycerides, natural or synthetic waxes, silicone gums and resins; proteins; or a mixture of these different agents.

The compositions according to the invention may be shampoos. Or they may be other types of hair care compositions (such as conditioners and mousses) and may be used before or after shampooing, before or after permanent-waving or between the reducing and fixing stages, and before or after bleaching or dyeing or straightening. To impart a conditioning benefit, the compositions of the invention when used in conjunction with hair dyes may also be used for the dyeing of keratinous fibers such as hair, in which case they contain oxidation dyes and/or direct dyes which are well known in the hair dyeing field. Dyes of this type are described, in particular, in Charles ZVIAK" Sciences des Traitements capillaires" [Hair treatment science] Ed. Masson, 1 988, the disclosure of which is hereby incorporated by reference. To impart a conditioning benefit, the compositions may also be used in conjunction with permanent wave agents for permanent-waving in which case they contain reducing agents or fixing or neutralizing agents, depending on whether the composition is used for reducing or fixing hair. Such products are described, in particular, in Charles ZVIAK "Sciences des Traitements capillaires" mentioned above.

These products generally take the form of emulsions or dispersions or solutions. They can also be in the form of fluid or thickened liquids, gels or creams. They may be used as they are or be diluted before use. They can also be packaged in a container under pressure and be delivered in spray, liquid, cream, gel or foam form.

The compositions of the invention are preferably aqueous.

Another subject of the invention is drawn to a process for the treatment of hair, comprising applying a composition as defined above to the hair to be treated and in optionally carrying out rinsing.

Ranges of Phytantriol and Ceramide in Compositions of the Invention.

Ceramide: about 0.001 to about 1.0 wt. %

Phytantriol about 0.001 to about 1.0 wt. %

Preferred wt. % ratios of Ceramide to Phytantriol range from about 0.5 to about 3.0.

The compositions of the invention are made as described below and by processes which are known to those skilled in the art. The compositions of the invention are made from starting materials which are known to those skilled in the art or which can be made by processes known to those skilled in the art.

Improved Properties of Compositions of the Invention

The compositions of this invention would provide for unexpected improvements in detangling and wet stage conditioning of hair can be evaluated by using the Instron combing method which is detailed in M. Garcia & J. Diaz, JSCC, Vol. 27, 1976, p379 which is hereby incorporated by reference. The compositions of this invention would provide for unexpected improvements in the conditioning properties of hair and this can be shown by salon blitz testing.

The examples which follow are intended to illustrate the invention, no limitation of the latter being, however, implied.

Non-limiting examples of the invention can be prepared as follows.

EXAMPLES

Example 1

Shampoo Example Containing Phytantriol/Ceramide Combination

| Ingredient | Wt. % |
| --- | --- |
| (1) Sodium Lauryl Ether Sulfate (25% Active) | 56.00 |
| (2) Carbopol 980 (2% aqueous solution) | 20.00 |
| (3) Cocamidopropyl betaine | 6.67 |
| (4) DC 1784 Dimethiconol Emulsion (50% Active) | 2.00 |
| (5) Propylene Glycol | 0.5 |
| (6) Jaguar C13S | 0.1 |
| (7) Phytantriol | 0.1 |
| (8) Ceramide A[1] | 0.25 |
| (9) Polyglucose | 0.25 |
| (10) Preservatives and Fragrance | 0.75 |
| (11) Sodium Chloride | 0.5 |
| (12) Sodium Hydroxide | 0.45 |
| (13) Water | q.s. |

[1]N-oleoyldihydrosphingosine

Preparation of Shampoo Example a. In Tank A introduce ingredient 1 b. Prepare Premix A by mixing ingredient 5 and ingredient 6 until ingredient 6 is well dispersed.

c. Add Premix A to Tank A and mix well.

d. Add Ingredients 12 and 2 to Tank A. Mix well and Heat Tank A to 60° C.

e. Prepare Premix B by combining ingredients 8 and 9 and heat to 60° C.

f. Mix Premix B until ingredients are fully melted.

g. Add Premix B into Tank A at 60° C.

h. Once fully mixed begin cooling contents of Tank A to 35–40° C.

i. Add ingredients 3 and 4 to Tank A and mix well.

k. Prepare Premix C by combining ingredients 7 and 10.

l. Add Premix C to Tank A and mix well.

m. Add remaining ingredients (11 and 12) to Tank A to bring batch to pH 5.7–6.3 and viscosity 4,000–7,000 cps.

Example 2

Conditioner Example Containing Phytantriol/Ceramide Combination

| Ingredient | Wt. % |
| --- | --- |
| (1) Stearamidoproyl Dimethylamine | 0.50 |
| (2) Citric Acid | 0.185 |
| (3) Propylene Glycol | 0.50 |
| (4) Dicetyldimonium Chloride | 2.10 |
| (5) Stearyl Alcohol | 1.0 |
| (6) Cetyl Alcohol | 3.25 |
| (7) Cyclomethicone | 1.8 |
| (8) Dimethicone | 0.10 |
| (9) Ceramide A[1] | 0.25 |
| (10) Polyglucose | 0.25 |
| (11) Phytantriol | 0.1 |
| (12) Preservatives and Fragrance | 0.75 |
| (13) Water | q.s. |

[1]N-oleoyldihydrosphingosine

Preparation of Conditioner Example a. Add ingredient 13 into Tank A and heat to 75–85° C.

b. Once Tank A achieves 75–85° C. add in ingredients 1, 2, 3, 4, 5, and 6. Mix well until completely melted.

c. Prepare Premix A by combining ingredients 9 and 10 and heating to 75–85° C.
d. Once Premix is completely melted add to Tank A.
e. Begin cooling Tank to 35–40° C.
f. Once Tank A is cooled to 35–40° C., then add ingredients 7 and 8 and mix well.
g. Prepare Premix B by combing ingredients 11 and 12.
h. Add Premix B to Tank A to complete the batch.

Hair is treated with the compositions of the invention by (1) applying water to said hair (or starting the process with hair that is damp because it has already been shampooed); (2) applying to said hair an effective amount of a composition of the invention; (3) rubbing said hair with the hands or a hair appliance such as a comb; and (4) rinsing said hair with water.

These compositions of the invention enhance conditioning as would be shown by salon blitz testing and Instron combing testing. The Instron combing test and combing force are as described in Garcia et al, *J. Soc. Cosmet. Chem.* 27:379(1976) which is hereby incorporated by reference.

What is claimed is:

1. A composition which comprises:

| Ingredient | Wt. % |
| --- | --- |
| (1) Sodium Lauryl Ether Sulfate (25% Active) | 56.00 |
| (2) Carbopol 980 (2% aqueous solution) | 20.00 |
| (3) Cocamidopropyl betaine | 6.67 |
| (4) DC 1784 Dimethiconol Emulsion (50% Active) | 2.00 |
| (5) Propylene Glycol | 0.5 |
| (6) Jaguar C13S | 0.1 |
| (7) Phytantriol | 0.1 |
| (8) Ceramide A[1] | 0.25 |
| (9) Polyglucose | 0.25 |
| (10) Preservatives and Fragrance | 0.75 |
| (11) Sodium Chloride | 0.5 |
| (12) Sodium Hydroxide | 0.45 |
| (13) Water | q.s.. |

[1]N-oleoyldihydrosphingosine

2. A composition which comprises:

| Ingredient | Wt. % |
| --- | --- |
| (1) Stearamidoproyl Dimethylamine | 0.50 |
| (2) Citric Acid | 0.185 |
| (3) Propylene Glycol | 0.50 |
| (4) Dicetyldimonium Chloride | 2.10 |
| (5) Stearyl Alcohol | 1.0 |
| (6) Cetyl Alcohol | 3.25 |
| (7) Cyclomethicone | 1.8 |
| (8) Dimethicone | 0.10 |
| (9) Ceramide A[1] | 0.25 |
| (10) Polyglucose | 0.25 |
| (11) Phytantriol | 0.1 |
| (12) Preservatives and Fragrance | 0.75 |
| (13) Water | q.s.. |

[1]N-oleoyldihydrosphingosine

* * * * *